(12) United States Patent
Potempa et al.

(10) Patent No.: US 6,190,670 B1
(45) Date of Patent: Feb. 20, 2001

(54) USE OF MCRP TO ENHANCE IMMUNE RESPONSES

(75) Inventors: Lawrence A. Potempa, Deerfield; James A. Radosevich, Rockford, both of IL (US)

(73) Assignee: Immtech International Inc., Vernon Hills, IL (US)

( * ) Notice: Under 35 U.S.C. 154(b), the term of this patent shall be extended for 0 days.

(21) Appl. No.: 09/376,628

(22) Filed: Aug. 18, 1999

Related U.S. Application Data

(60) Provisional application No. 60/128,888, filed on Apr. 2, 1999.

(51) Int. Cl.$^7$ .......................... A61K 39/00; A61K 39/385

(52) U.S. Cl. .................... 424/278.1; 424/184.1; 424/185.1; 514/885

(58) Field of Search ............................ 424/184.1, 277.1, 424/278.1, 185.1; 514/2, 885

(56) References Cited

U.S. PATENT DOCUMENTS

| | | |
|---|---|---|
| 4,857,314 | 8/1989 | O'Connor et al. . |
| 5,272,258 | 12/1993 | Siegel et al. . |
| 5,283,238 | 2/1994 | Potempa et al. . |
| 5,405,832 | 4/1995 | Potempa . |
| 5,474,904 | 12/1995 | Potempa et al. . |
| 5,547,931 | 8/1996 | Potempa . |
| 5,585,349 | 12/1996 | Potempa . |
| 5,593,897 | 1/1997 | Potempa et al. . |
| 5,662,907 | * 9/1997 | Kubo et al. . |
| 5,858,399 | 1/1999 | Lanza et al. . |
| 5,874,238 | 2/1999 | Potempa et al. . |
| 5,939,529 | 8/1999 | Potempa . |
| 6,051,415 | 4/2000 | Potempa . |

FOREIGN PATENT DOCUMENTS

WO93/10799 * 6/1993 (WO) .
WO93/21944 * 11/1993 (WO) .

OTHER PUBLICATIONS

Bareika et al., "Changes in C–Reactive Protein Levels in Rabbit Sera Following Intraarticular Injection of Chymopapain," 45th Annual Meeting, Orthopaedic Research Society, Feb. 1–4, 1999, Anaheim, California.
Bray et al., *J. Immunol.*, 140(12):4271–4278 (1988).
Bray et al., *Clin. Immunol. Newsletter* 8, pp. 137–140 (1987).
Chu et al., *Proc. Amer. Acad. Cancer Res.*, 29, 371a (1988).
Chu et al., *Proc. Amer. Acad. Cancer Res.*, 28, 344a (1987).
Ciliberto et al., *Nucleic Acids Res.*, 15, 5895 (1987).
Crump et al., "Bacterial Expression of Mutant Human C–Reactive Protein Subunit," Annual Meeting of the Society for Industrial Microbiology, Research Triangle Park, North Carolina, Aug. 3–9, 1996 (Abstract).
Crump et al., "Bacterial Expression of Mutant Human C–Reactive Protein Subunit" Annual Meeting of the Society for Industrial Microbiology, Research Triangle Park, North Carolina, Aug. 3–9, 1996.
de Beer et al., *J. Immunol. Meth.*, 50:17–31 (1982).
Diehl et al., "Effects of the Modified Form of C–Reactive Protein on Human Tumor Cells" Cancer Research AMFR Meeting, 1998.
Diehl et al., "Cellular effects of the modified form of C–reactive protein (mCRP) on tumor cells" 17th Int'l Cancer Congress, Rio de Janeiro, Brazil, Aug. 24–28, 1998.
Hu et al., *Biochem.*, 25, 7834–39 (1986).
Hu et al., *J. Biol. Chem.*, 263, 1500–1504 (1988).
Kabat et al., "Antiretroviral Activity of a Recombinant Modified C–Reactive Protein" Twenty–First AIDS Clinical Trials Group Meeting, Sheraton Washington Hotel, Washington, D.C., Jul. 27–31, 1996.
Kilpatrick et al., *Immunol. Res.*, 10:43–53 (1991).
Kinoshita et al. *Biochemistry*, 28:9840–9848 (1989).
Kolb–Bachofen, *Immunobiol.*, 183:133–145 (1991).
Kresl et al. *Int'l J. Biochem. Cell Biol.*, 30, 1415–1426 (1998).
Kresl et al., *Tumor Biol.*, 20:72–87 (1999).
Lei et al., *J. Biol. Chem.*, 260, 13377–83 (1985).
Motie et al., *J. Immunol.*, 156:4435–4441 (1996).
Motie et al., *Drug Metabolism and Disposition*, 26(10):977–981 (1998).
Potempa et al., *Inflammation*, 12, 391–405 (1988).
Potempa et al., *Protides Biol. Fluids*, 34, 287–290 (1986).
Potempa et al., *Proc. Amer. Acad. Cancer Res.*, 28, 344a (1987).

(List continued on next page.)

Primary Examiner—David Saunders
Assistant Examiner—Amy DeCloux
(74) *Attorney, Agent, or Firm*—Sheridan Ross P.C.

(57) ABSTRACT

The invention provides a method of enhancing an immune response to an immunogen in an animal. The method comprises administering to the animal an effective amount of the immunogen and an effective amount of a modified C-reactive protein (mCRP) or a mutant-mCRP. The invention also provides a vaccine and a method of producing this vaccine. The vaccine comprises an immunogen and an mCRP or a mutant-mCRP in a pharmaceutically-acceptable vehicle. The invention further provides a kit for immunizing an animal to an immunogen comprising (1) a container holding the immunogen and a container holding an mCRP or a mutant-mCRP or (2) a container holding the immunogen and an mCRP or a mutant-mCRP. The invention also provides a method of elicing an immune response to a hapten in an animal. The method comprises administering to the animal an effective amount of the hapten in association with an an effective amount of an mCRP or a mutant-mCRP. The invention further provides a vaccine and a method of producing this vaccine. The vaccine comprises a hapten and an mCRP or a mutant-mCRP in a pharmaceutically-acceptable vehicle. Finally, the invention provides a kit for immunizing an animal to a hapten comprising a container holding the hapten and an mCRP or a mutant-mCRP.

2 Claims, 4 Drawing Sheets

OTHER PUBLICATIONS

Potempa et al., *Mol. Immunol.*, 24, 531–541 (1987).
Potempa et al., *Mol. Immunol.*, 20, 1165–1175 (1983).
Potempa et al., *Proceedings of the International Congress on Membranes and Membrane Processes*, 1:169–171 (1990).
Potempa et al., *Clinical Materials*, 11:105–117 (1992).
Potempa et al., *Exper. Hematol.*, 24:258–264 (1996).
Potempa et al., *FASEB J.*, 10:1332a (1996) (Abstract #1918 and presentation materials).
Potempa et al., "In vitro studies of recombinant human modifed C reactive protein, an active new agent against HIV disease" #B01 Hong Kong AIDS Conference 1996.
Potempa et al., "Phase I/II clinical trial of recombinant human modified C reactive protein, an active new agent against HIV disease" #B02 Hong Kong AIDs Conference 1996.
Potempa et al., "Biological activity and clinical safety of human modified C–reactive protein, an active new agent against cancer" #H41.1 Hong Kong Int'l Cancer Congress 1996.
Radosevich et al., *Cancer Res.*, 45:5808–5812 (1985).
Radosevich et al., *FASEB J.*, 10:1466a (1996) Abstract.
Rees et al., *Clin. Immunol. and Immunopathol.*, 48:95–107 (1988).
Samberg et al., *Cell. Immunol.*, 116:86–98 (1988).
Samols and Hu, *Protides Biol. Fluids*, 34, 263–66 (1986).
Schneider et al., *FASEB J.*, 12:185a (1998) (abstract and presentation materials).
Stein et al., *Immunobiology*, Abstract V.15 (1999).
Syin et al., *J. Biol. Chem.*, 261, 5473–79 (1986).
Tucci et al., *J. Immunol.*, 131, 2416–2419 (1983).
Vaith et al., *Int Arch Allergy Immunol*, 111:107–117 (1996).
Volanakis et al., *J. Immunol.*, 113:9–17 (1978).
Whitehead et al., *Science*, 221, 69–71 (1983).
Whitehead et al., *Biochem. J.*, 266, 283–90 (1990).
Woo et al., *J. Biol. Chem.*, 260, 13384–88 (1985).
Ying et al., *J. Immunol.*, 143:221–228 (1989).
Zeller et al., *Fed. Proc.*, 46, 1033a (1987).

* cited by examiner

USE OF MCRP TO ENHANCE IMMUNE RESPONSES

This application claims benefit of provisional application No. 60/128,888, filed Apr. 12, 1999.

FIELD OF THE INVENTION

The invention is concerned with enhancing immune responses. In particular, it has been discovered that modified C-reactive protein (mCRP) and mutant-mCRP can be used to enhance immune responses to immunogens and to elicit an immune response to haptens.

BACKGROUND OF THE INVENTION

During injury, invasion of pathogens, or other forms of tissue damage, higher vertebrates implement a cascade of biochemical, immune and inflammatory reactions collectively termed the acute phase response. The inflammation results in an increase in blood flow and the delivery of important factors to the affected site. These factors act to limit microbial growth, reduce tissue damage, and aid in the removal of damaged tissue. The acute phase response is a primitive, nonspecific mechanism which reacts quickly prior to the development of the specific processes of humoral and cellular immunity.

C-reactive protein (CRP) has long been recognized as an important acute phase response protein, and its concentration in serum may increase as much as 1,000-fold during the acute phase response. CRP is a pentamer consisting of five identical subunits, each having a molecular weight of about 23,500. The pentameric form of CRP is sometimes referred to as "native CRP."

In about 1983, another form of CRP was discovered which is referred to as "modified-CRP" or "mCRP." The formation of mCRP from native CRP involves the dissociation of native CRP into its subunits which also undergo a change in conformation. As a result, mCRP expresses antigenicity which is distinct from that of native CRP (referred to as "neo-CRP antigenicity"), and antibodies are available which can distinguish mCRP from native CRP (see, e.g., U.S. Pat. No. 5,272,258 and Potempa et al., *Mol. Immunol.*, 24, 531–541 (1987)). The conversion of native CRP into mCRP is irreversible (the subunits do not reassemble into native CRP). Kresl et al., *Int'l J. Biochem. Cell Biol.*, 30, 1415–1426 (1998).

It has been reported that mCRP can influence the development of monocyte cytotoxicity, improve the accessory cell function of monocytes, potentiate aggregated IgG-induced phagocytic cell oxidative metabolism, and increase the production of interleukin-1, prostaglandin E and lipoxygenase products by monocytes. Potempa et al., *Protides Biol. Fluids*, 34, 287–290 (1987); Potempa et al., *Inflammation*, 12, 391–405 (1988); Potempa et al., *Proc. Amer. Acad. Cancer Res.*, 28, 344a (1987); Chu et al., *Proc. Amer. Acad. Cancer Res.*, 28, 344a (1987); Zeller et al., *Fed. Proc.*, 46, 1033a (1987); Chu et al., *Proc. Amer. Acad. Cancer Res.*, 29, 371a (1988). It is also known that mCRP can be used to treat viral infections, bacterial infections, endotoxic shock and cancer. See U.S. Pat. Nos. 5,283,238, 5,405,832, 5,474,904, and 5,585,349. It is further known that mCRP stimulates thrombocytopoiesis and the maturation of megakaryocytes and that it can be used to treat thrombocytopenia. See U.S. Pat. No. 5,547,931. Finally, it is known that mCRP binds immune complexes and aggregated immunoglobulin and can, therefore, be used to remove immune complexes and aggregated immunoglobulin from fluids and to quantitate immune complexes. See U.S. Pat. No. 5,593,897. It should be noted that mCRP differs from native CRP in its biological activities. See, e.g., the patents listed above.

SUMMARY OF THE INVENTION

The invention provides a method of enhancing an immune response to an immunogen in an animal. The method comprises administering to the animal an effective amount of the immunogen and an effective amount of a modified C-reactive protein (mCRP) or a mutant-mCRP, as further defined below.

The invention further provides a vaccine comprising an immunogen and an mCRP or a mutant-mCRP in a pharmaceutically-acceptable vehicle. The invention also provides a method of producing this vaccine. The method comprises combining the immunogen and an mCRP or a mutant-mCRP.

The invention further provides a kit for immunizing an animal to an immunogen. The kit may comprise a container holding the immunogen and a container holding an mCRP or a mutant-mCRP. Alternatively, the kit may comprise one container holding both the immunogen and the mCRP or mutant-mCRP.

In addition, the invention provides a method of eliciting an immune response to a hapten in an animal. The method comprises administering to the animal an effective amount of the hapten in association with an effective amount of an mCRP or a mutant-mCRP.

The invention further provides a vaccine comprising a hapten and an mCRP or a mutant-mCRP in a pharmaceutically-acceptable vehicle. The invention also provides a method of producing this vaccine. The method comprises combining the hapten and an mCRP or a mutant-mCRP.

Finally, the invention provides a kit for immunizing an animal to a hapten. The kit comprises a container holding the hapten and the mCRP or the mutant-mCRP.

DETAILED DESCRIPTION OF THE PRESENTLY PREFERRED EMBODIMENTS OF THE INVENTION

Figure 1A:
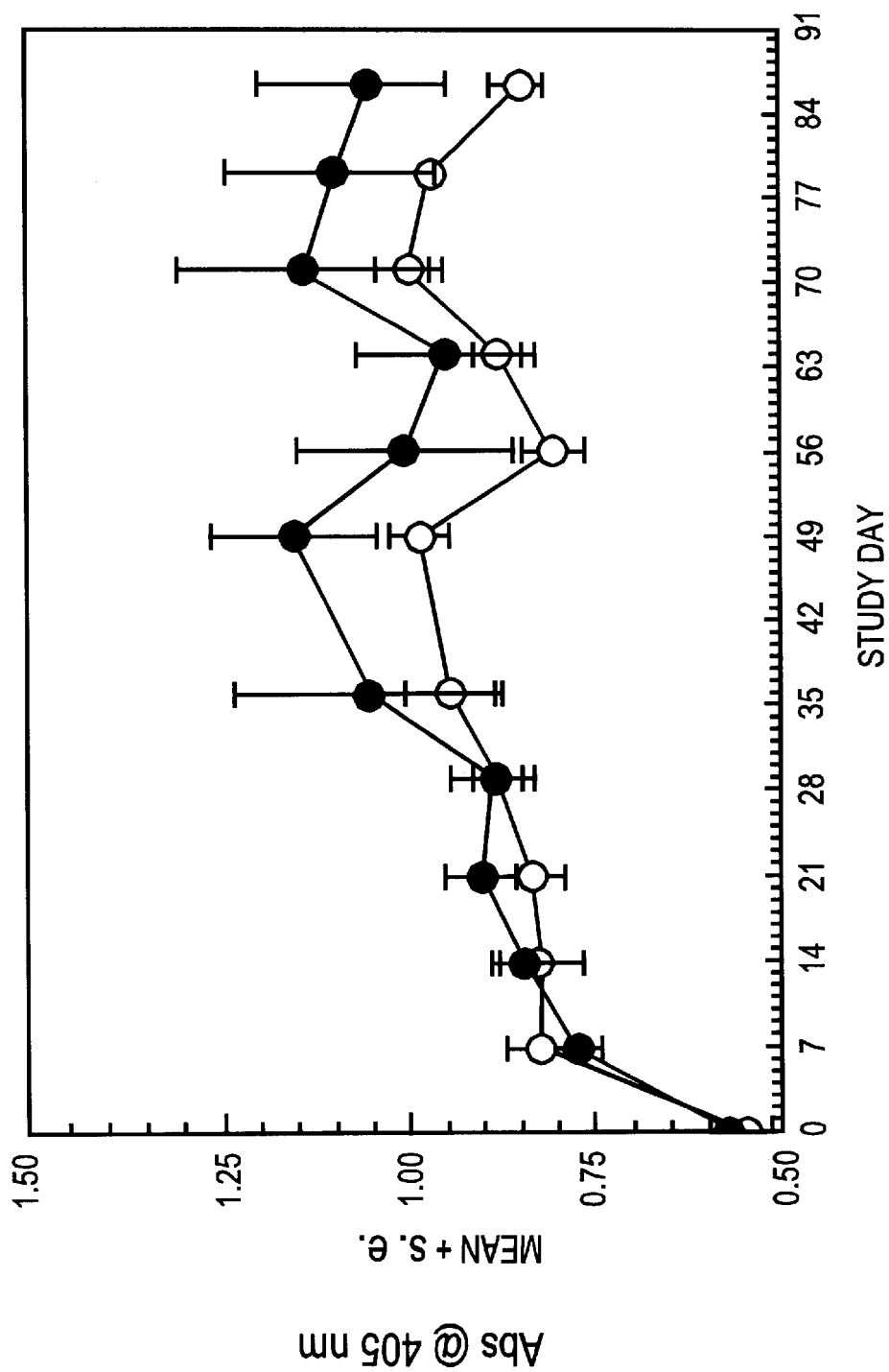
FIG. 1A: Graph of absorbance at 405 nm versus study day for mice immunized with human lung adenocarcinoma A-549 peptides with a mutant-mCRP (treated group) or with saline (no mutant-mCRP; control group). Open circles—control group; closed circles—mutant-mCRP-treated group.

Modified-CRP can be prepared by using native CRP as the starting material. The native CRP used for preparation of mCRP can be obtained from natural sources (e.g., serum, plasma, pleural fluid or ascites fluid). Methods of isolating native CRP from natural sources are known in the art and are described, for example, by Volanakis et al., *J. Immunol.,* 113:9–17 (1978); de Beer et al., *J. Immunol. Meth.,* 50:17–31 (1982); Potempa et al., *Mol. Immunol.,* 24:531–541 (1987). CRP is preferably isolated from serum, plasma, pleural fluid, or ascites fluid by calcium-dependent affinity chromatography using phosphorylcholine-substituted BioGel® A 0.5 m (an agarose-based resin obtained from BioRad Laboratories, Richmond, Calif.). See, Potempa et al., *Mol. Immunol.,* 24:531–541 (1987). Using this isolation method, CRP can be obtained which is about 99% pure. Partially purified CRP may be obtained from commercial sources, such as Western States Plasma (Fallbrook, Calif.).

Native CRP can also be produced by recombinant DNA techniques. Genomic and cDNA clones coding for human, mouse, and rabbit CRP have been isolated and sequenced. Tucci et al., *J. Immunol.,* 131, 2416–2419 (1983); Whitehead et al., *Science,* 221, 69–71 (1983); Lei et al., *J. Biol. Chem.,* 260, 13377–83 (1985); Woo et al., *J. Biol. Chem.,* 260, 13384–88 (1985); Hu et al., *Biochem.,* 25, 7834–39 (1986); Samols and Hu, *Protides Biol. Fluids,* 34, 263–66 (1986); Syin et al., *J. Biol. Chem.,* 261, 5473–79 (1986); Ciliberto et al., *Nucleic Acids Res.,* 15, 5895 (1987); Hu et al., *J. Biol. Chem.,* 263, 1500–1504 (1988); Whitehead et al., *Biochem, J.,* 266, 283–90 (1990). Further, there is substantial homology between the amino acid sequences of CRPs from different species. For instance, there is from about 50% to about 80% sequence homology between CRPs from various mammalian species. Hu et al.,*Biochem.,* 25,7834–39 (1986); Whitehead et al., *Biochem, J.,* 266,283–90 (1990); and Kilpatrick et al., *Immunol. Res.,* 10, 43–53 (1991). Given the substantial homology between CRPs from different species, probes can readily be prepared from the known clones so that genomic and cDNA clones can be isolated which code for CRP from other species. Methods of preparing such probes and isolating genomic and cDNA clones are well known. See, e.g., Lei et al., *J. Biol. Chem.,* 260, 13377–83 (1985); Woo et al.,*J. Biol. Chem.,* 260, 13384–88 (1985); Hu et al., *Biochem.,* 25, 7834–39 (1986); Hu et al., *J. Biol. Chem.,* 263, 1500–1504 (1988); Whitehead et al., *Biochem. J,* 266,283–90 (1990). To obtain native CRP, eukaryotic host cells, preferably mammalian host cells, should be used for the expression of the CRP clone. See Samols and Hu, *Protides Biol. Fluids,* 34, 263–66 (1986); Hu et al., *J. Biol. Chem.,* 263, 1500–1504 (1988).

Methods of making mCRP from native CRP are known in the art (See, e.g., Potempa et al., *Mol. Immunol,* 20, 1165–1175 (1983); Potempa et al., *Mol. Immunol.,* 24, 531–541 (1987)). For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11–12. Finally, mCRP can be produced by heating CRP above 50° C., for a time sufficient to cause denaturation (preferably at 63° C. for 2 minutes), in the absence of calcium or in the presence of a chelator.

Monomeric preCRP, produced by cell-free translation of DNA coding for it, expresses neo-CRP antigenicity. preCRP is a precursor protein consisting of a signal or leader sequence attached to the N-terminus of the CRP subunit. During normal processing, the signal or leader sequence is cleaved from the preCRP molecules to produce mature CRP subunits which assemble into pentameric native CRP. This normal processing and assembly occur in eukaryotic cells. See Tucci et al.,*J. Immunol.,* 131,2416–2419 (1983); Samols and Hu, *Protides Biol. Fluids,* 34, 263–66 (1986); Hu et al., *J. Biol. Chem.,* 263, 1500–1504 (1988). Therefore, mCRP can be prepared directly by recombinant DNA techniques by selecting conditions so that the CRP subunits are not assembled into pentameric native CRP. This can be accomplished by expressing a desired genomic or cDNA clone in prokaryotic cells (referred to herein as "recombinant-mCRP" or "$r_m$CRP"). Recombinant-mCRP produced in prokaryotic cells consists of CRP subunits, preCRPs and/or fragments of the subunits and preCRPs. The CRP subunits and preCRPs may have slightly altered N-terminal and C-terminal sequences which reflect or assist their production in prokaryotic cells. For instance, they may have methionine as the N-terminal amino acid.

Therefore, as used herein, the terms "modified-CRP" and "mCRP" mean preCRPs or subunits of CRP, in free or aggregated form, which express neo-CRP antigenicity. The terms comprise all of those forms of mCRP described above, including CRP subunits and preCRPs having slightly altered N-terminal and C-terminal sequences which reflect or assist their production in prokaryotic cells. Neo-CRP antigenicity can be detected using antibodies specific for mCRP (see, e.g., U.S. Pat. No. 5,272,258 and Potempa et al., *Mol. Immunol.,* 24, 531–541 (1987)) in standard immunoassays. Further, given the substantial homology between the amino acid sequences of CRPs from different species, it is expected that mCRP from any species will be effective in the practice of the invention.

To avoid the aggregation of the CRP subunits and pre-CRPs that generally occurs when DNA coding for preCRP is expressed in prokaryotic cells, mutant CRP subunits and preCRPs have been developed. These mutant CRP subunits and preCRPs contain one or more amino acid changes that produce CRP subunits and preCRPs that are less likely to aggregate when produced in prokaryotic cells. The amino acid(s) added, deleted and/or replaced are also chosen so that the mutant protein retains the neo-CRP antigenicity characteristic of mCRP.

Suitable amino acid changes include the deletion or replacement of at least one, preferably all, of the cysteines in an unmutated CRP subunit or unmutated preCRP. CRP subunits contain two cysteines and preCRP's contain three cysteines, and it is believed that some of these cysteines form intermolecular disulfide bonds, thereby contributing to the formation of non-dissociable cross-linked aggregates. Therefore, one or more, preferably all, of these cysteines are desirably deleted or replaced. When the cysteines are replaced with other amino acids, they are preferably replaced with glycine, alanine, valine, leucine, isoleucine, serine, threonine or methionine, but any amino acid can be used. Most preferred is substitution with alanine. Lysine and derivatized lysine residues may also contribute to non-dissociable cross-linking. Accordingly, suitable amino acid changes may also include the deletion or replacement of at least one of the lysines in an unmutated CRP subunit or unmutated preCRP. As a result of the amino acid changes in them, the mutant proteins are easier to purify with much higher yields than unmutated CRP subunits or unmutated preCRP's.

Not all of the amino acid additions, deletions and replacements need contribute to the reduced likelihood of forming non-dissociable aggregates as long as the combined effect of all the changes is a reduction in intermolecular nondissociable cross-linking. For instance, the recombinant DNA manipulations used to produce the mutant proteins may result in amino acids being added at the amino or carboxy terminal ends of the CRP subunit. This is acceptable as long as these amino acids do not contribute to the production of nondissociable aggregates. In addition, some of the amino acid changes may be made for other purposes. For instance, it is desirable to make amino acid changes which increase the solubility of the resultant mutant protein in aqueous media, since a more soluble mutant protein is easier to purify and process. Suitable amino acid changes to increase the solubility include deleting one or more hydrophobic amino acids, replacing one or more hydrophobic amino acids with charged amino acids, adding one or more charged amino acids, or combinations of these changes. However, for the reasons stated above, it may be desirable to avoid the addition of lysine residues. Aqueous media include water, saline, buffers, culture media, and body fluids. As another example, amino acid changes can be made for the purpose of providing for the association of an immunogen or a hapten with the mutated CRP subunit or preCRP (see below).

The mutant proteins can be prepared by expression of DNA coding for them in transformed host cells. DNA coding for a mutant protein can be prepared by in vitro mutagenesis of a known or newly-isolated CRP genomic or cDNA clone or can be chemically synthesized. In vitro mutagenesis techniques are conventional and well known. Particularly preferred is site-directed mutagenesis using polymerase chain reaction (PCR) amplification. See, e.g., U.S. Pat. No. 5,547,931. The following references described other site-directed mutagenesis techniques which can be used to produce DNA coding for a mutant protein: *Current Protocols In Molecular Biology,* Chapter 8 (Ansubel ed. 1987); Smith & Gilliam, *Genetic Engineering Principles And Methods,* 3, 1–32 (1981); Zoller & Smith, Nucleic Acids Res., 10, 6487–6500 (1982); Zoller et al., *Methods Enzymol,* 100, 468–500 (1983); Zoller & Smith, *DNA,* 3, 479–88 (1984); Brake et al., *Proc. Natl. Acad, Sci. USA,* 81, 4642–46 (1984); *Bio/Technology, pages* 636–39 (July 1984); Botstein et al., *Science,* 229, 1193 (1985); Kunkel et al., *Methods. Enzymol.,* 154, 367–82 (1987).

DNA coding for a mutant protein of the invention can also be prepared by chemical synthesis. Methods of chemically synthesizing DNA having a specific sequence are well-known in the art. Such procedures include the phosphoramidite method (see, e.g., Beaucage and Caruthers, *Tetrahedron Letters,* 22, 1859 (1981); Matteucci and Caruthers, *Tetrahedron Letters,* 21, 719 (1980); and Matteucci and Caruthers, *J. Amer. Chem. Soc.,* 103, 3185 (1981)) and the phosphotriester approach (see, e.g., Ito et al., *Nucleic Acids Res.,* 10, 1755–69 (1982)).

Therefore, as used herein, the term "mutant-mCRP" means preCRPs or subunits of CRP having a sequence mutated as described above which express neo-CRP antigenicity. As noted above, neo-CRP antigenicity can be detected using specific antibodies in standard immunoassays. Further, given the substantial homology between the amino acid sequences of CRPs from different species, it is expected that mutant-mCRPs derived from the preCRPs or CRP subunits of any species will be effective in the presently claimed invention.

For a detailed description of the physical and chemical properties, biological activities, and methods of making mCRP, including $r_m$CRP, and mutant-mCRP, and antibodies to neo-CRP antigenicity, see U.S. Pat. Nos. 5,272,258, 5,283,238, 5,405,832, 5,474,904, 5,547,931, 5,585,349, 5,593,897, and 5,874,238, published PCT application WO 94/18999, and U.S. patent applications Ser. Nos. 08/480,270, 08/548,974, 08/549,013 and 08/767,795, the complete disclosures of which are incorporated herein by reference.

Fragments of CRP subunits and preCRPs, having a native or mutant sequence, may have the same activities described herein for mCRP and mutant-mCRP, and the use of such fragments is considered to come within the scope of the present invention. It is also believed that proteins substantially homologous to CRP will have the activities described herein for mCRP, and such proteins are also considered to come within the scope of the present invention.

The present invention is based on the discovery that mCRP and mutant-mCRP can act as adjuvants. As used herein, the term "adjuvant" means a substance that non-specifically enhances the immune response to an immunogen. "Immune response" means the specific humoral or cell-mediated response to an immunogen. Thus, antibody production or cell-mediated immunity is more vigorous in an animal receiving mCRP or mutant-mCRP than it is when the immunogen is given without the adjuvant. The fact that an immune response is enhanced can be determined by comparative testing (e.g., administering an immunogen with and without mCRP or mutant-mCRP under otherwise identical conditions and measuring the immune response, e.g., measuring antibody titers). In addition, the immune response may be modified qualitatively (e.g., antibodies of different immunoglobulin classes may be stimulated).

Thus, mCRP or mutant-mCRP can be used to enhance an immune response to an immunogen in any species of animal that is capable of an immune response. Preferably, the animal is a mammal, such as a rabbit, goat, dog, cat, horse or human. The mCRP or mutant-mCRP used as the adjuvant in a particular species of animal may be from the same species or a different species of animal. For instance, when the animal to be immunized is a goat, goat mCRP, human mCRP, or mutant-mCRP derived from goat or human pre-CRPs or CRP subunits could be used as the adjuvant. However, to avoid an immune reaction to the adjuvant itself, mCRP from the same species that is to be immunized should be used. For instance, when it is desired to elicit an immune response to an immunogen in a goat, goat mCRP should be used as the adjuvant.

As used herein, an "immunogen" is any substance which stimulates an immune response (humoral immunity or cell-mediated immunity) in an animal. Immunogens are either antigens or haptens that have been modified to be immunogenic.

Antigens are substances that elicit a specific immune response when introduced into an animal. An antigen may contain one or more antigenic determinants or epitopes. Antigens include polysaccharides, lipids, lipopolysaccharides, proteins, glycoproteins, lipoproteins, nucleoproteins, peptides, oligonucleotides and nucleic acids. Specific immunogens include immunoglobulins, coagulation factors, peptide and protein hormones (e.g., insulin, gonadotropin, somatotropin), interleukins, interferons, other cytokines, peptides comprising a tumor-specific epitope (i.e., an epitope found only on a tumor-specific protein), peptides containing a sperm-specific epitope (i.e., an epitope found only on a sperm-specific protein), DNA, RNA, cells (e.g., red blood cells), cell-surface molecules (e.g., CD antigens, integrins, cell receptors), microorganisms (viruses, bacteria, molds, and fungi, which may be intact, lysed, ground, or otherwise fragmented), fragments, portions, components, or products of microorganisms, etc.

Haptens are substances that do not initiate an immune response when introduced by themselves into an animal. Generally, haptens are small molecules of molecular weight less than about 1 kD. Haptens include small organic molecules (e.g., digoxin, heroin, cocaine, morphine, mescaline, lysergic acid, tetrahydrocannabinol, cannabinol, steroids, pentamidine, biotin) and small peptides (2–4 amino acids). To be immunogenic, haptens must be modified. This is generally accomplished by coupling haptens to an immunogenic carrier.

Suitable carriers are compounds capable of stimulating an immune response to haptens coupled to them in a host animal. Many such carriers are well-known. For instance, the carrier may be a high molecular weight compound. Suitable high molecular weight compounds include proteins, polypeptides, carbohydrates, polysaccharides, lipopolysaccharides, nucleic acids, and the like of sufficient size and immunogenicity. Preferred high molecular weight compounds are proteins and polypeptides. Suitable immunogenic carrier proteins and polypeptides will generally have molecular weights between 4,000 and 10,000,000, and preferably greater than 15,000. Such suitable carriers include proteins such as albumins (e.g., bovine serum albumin, ovalbumin, human serum albumin), immunoglobulins, thyroglobulins (e.g., bovine thyroglobulin), hemocyanins (e.g., Keyhole Limpet hemocyanin), toxins (e.g., diptheria toxoid, tetanus toxoid) and polypeptides such as polylysine or polyalaninelysine.

Methods of coupling haptens to carriers are well known. For instance, peptides may be coupled to a carrier with conjugating reagents such as glutaraldehyde, a water soluble carbodiimide such as 1-(3-dimethylaminopropyl)-3-ethylcarbodiimide hydrochloride (ECDI), N-N-carbonyldiimidazole, 1-hydroxybenzotriazole monohydrate, N-hydroxysuccinimide, 6-maleimidocaproyl-N-hydroxysuccinimide, n-trifluoroacetylimidazole cyanogen bromide, 3-(2'-benzothiazolyl-dithio)propionate succinimide ester hydrazides or affinity labeling methods. See also *Pierce Handbook and General Catalog* (1989) for a list of possible coupling agents. The number of peptides attached to the high molecular weight carrier is called the "epitopic density." The epitopic density can range from 1 to the number of available coupling groups on the carrier molecule. The epitopic density on a particular carrier will depend upon the molecular weight of the carrier and the density and availability of coupling sites. Preferably, only high molecular weight carriers having an epitopic density of at least 15 peptides per molecule are used in the practice of the invention.

To couple a small organic molecule hapten to a carrier protein, cross-linking chemical reagents can be used. Peeters, et al., *J. Immunol. Methods*, 120, 133–143 (1989); Pauillac, et al., *J. Immunol. Methods*, 220, 105–114 (1998); Kitagawa, *J. Biochem.*, 94, 1165–1172 (1983); Bauminger and Wilchek, *Methods Enzymol.*, 70, 151–159 (1980). One approach utilizes water-soluble NHS-ester maleimide heterobifunctional cross-linking reagent sulfo-MBS (Pierce Chemical Co., Rockford, Ill.). Amino functions on the hapten are covalently attached to the cross-linking reagent to form an active intermediate. This activated intermediate can be linked to a carrier molecule (such as ovalbumin) which has been modified with a group-specific modifying agent (such as 2-iminothiolane, which introduces additional free sulfhydryl groups on the carrier protein). This modification increases the density of reactive sites on the carrier so that, when the activated hapten intermediate is mixed with the modified carrier, a covalent linkage of hapten to carrier can occur at a high hapten-to-carrier molar ratio. A high hapten-to-carrier molar ratio is preferred to elicit a strong immune response to the immunogen. Other methods of coupling small organic haptens to carriers are known. See, e.g., *Catalog And Handbook* (1994–1995) and *Products Catalog* (1997), Pierce Chemical Co., Rockford, Ill.

Additional references concerning conventional high molecular weight immunogenic carrier materials and techniques for coupling haptens thereto are: Erlanger, *Methods In Enzymology*, 70, 85–104 (1980); Makela and Seppala, *Handbook of Experimental Immunology* (Blackwell 1986); Parker, *Radioimmunoassay of Biologically Active Compounds* (Prentice-Hall 1976); Butler *J. Immunol. Meth.*, 7, 1–24 (1974); Weinryb and Shroff, *Drug. Metab. Rev.*, 10, 271–83 (1979); Broughton and Strong, *Clin. Chem.*, 22, 726–32 (1976); Playfair et al., *Br. Med. Bull.*, 30,24–31 (1974); U.S. Pat. Nos. 4,990,596 and 4,782,136.

In one embodiment of the invention, the immunogen comprises a peptide having a sequence which includes a B-cell epitope linked to a peptide having a sequence which includes a T-cell epitope. Methods of identifying B-cell epitopes of a protein are known. See O'Hern and Goldberg, in *Techniques In Protein Chemistry IV*, pages 481–490 (1993); O'Hern and Goldberg, *Proceed. Intern. Symp. Control Rel. Bioact. Mater.*, 20, 394–395 (1993). Three criteria are essential for immunogenicity: a size greater than 10 amino acids; surface accessibility of the sequence; and hypervariability (degree of foreignness). See O'Hern and Goldberg, in *Techniques In Protein Chemistry IV*, pages 481–490 (1993); O'Hern and Goldberg, *Proceed. Intern. Symp. Control Rel. Bioact. Mater.*, 20, 394–395 (1993). Methods of identifying T-cell epitopes are also known. See, O'Hern and Goldberg, in *Techniques In Protein Chemistry IV*, pages 481–490 (1993); O'Hern and Goldberg, *Proceed. Intern. Symp. Control Rel. Bioact. Mater.*, 20, 394–395 (1993). The three criteria for selection of a T-cell epitope are: a size of 8–12 amino acids; hypervariability; and one or more representations of the tetrapeptide motif previously reported to be associated with T-cell epitopes. O'Hern and Goldberg, in *Techniques In Protein Chemistry IV*, pages 481–490 (1993); O'Hern and Goldberg, *Proceed. Intern. Symp. Control Rel. Bioact. Mater.*, 20, 394–395 (1993). Most preferably, the peptide has a sequence comprising the sequence of a promiscuous T-cell epitope. A promiscuous T-cell epitope is a T-cell epitope that is recognized by individuals of several different major histocompatability (MHC) types. Promiscuous T-cell epitopes are known. See, Ho et al., *Eur. J. Immunol.*, 20, 477–483 (1990); Kaumaya, et al., *J. Molec. Recog.*, 6, 81–94 (1993). A peptide which has a sequence comprising the sequence of a T-cell epitope may include other sequences linked to the N-terminal or C-terminal of the T-cell epitope. In particular, additional amino acids may be provided to link the B-cell epitope to the T-cell epitope. These linking amino acids should form a four-residue $\beta$-turn, based on examination of 33 patterns in native proteins that code for $\alpha\alpha$ corners. Efimov, *FEBSLett.*, 166, 33 (1984); Kaumaya et al., *Biochemistry*, 29, 13–23 (1990). Peptides comprising a B-cell epitope may be coupled to a peptide comprising a T-cell epitope in the same manner as described above for coupling haptenic peptides to high molecular weight proteins and polypeptides to form the immunogen. However, such immunogens are preferably synthesized as a single peptide. Methods of synthesizing peptides are well known in the art. For instance, peptides can be synthesized by solid phase synthesis techniques or by recombinant DNA techniques.

To enhance an immune response, an effective amount of an mCRP or a mutant-mCRP is administered to an animal.

The mCRP or mutant-mCRP may be administered in association with the immunogen, or the immunogen and the mCRP or mutant-mCRP may be administered separately. When the immunogen and the mCRP or mutant-mCRP are administered separately, they may be administered at separate sites, by separate routes and/or at different times. Preferably, the immunogen and the mCRP or mutant-mCRP are administered at approximately the same time and, most preferably, are administered in association with each other.

An immunogen may be associated with an mCRP or a mutant-mCRP in a variety of ways. For instance, the immunogen and the mCRP or mutant-mCRP can simply be mixed together and administered simultaneously to the animal.

In such mixtures, neutral immunogens will associate with mCRP as a result of hydrophobic interactions to form complexes, if the immunogen and mCRP are held in contact for a time sufficient (such times can be determined empirically) to allow the complexes to form. The contacting of the immunogen and the mCRP may take place in a solution of low ionic strength or a solution of high ionic strength (see definitions below). A neutral immunogen can be associated with a mutant-mCRP in this same way, provided that the amino acid changes in the mutant-mCRP do not substantially change the hydrophobicity of the mutant-mCRP as compared to mCRP. Since mCRP has strong hydrophobic characteristics, neutral immunogens can be complexed with most mutant-mCRPs in this manner. Anionic and cationic immunogens can be complexed as a result of ionic interactions with an mCRP which has been altered to be more positively or negatively charged. Methods of derivatizing proteins to change their charge are well known. See, e.g., Means and Feeney, *Chemical Modification Of Proteins* (Holden-Day Inc., San Francisco, Calif., 1971). For instance, positively-charged groups or negatively-charged groups could be attached to the mCRP. Alternatively, the mCRP could be chemically treated to change its charge (e.g., by changing positively-charged residues to negatively-charged residues). In another alternative, mutant-mCRPs mutated to be more positively charged or more negatively charged could be used. The use of complexes formed as a result of hydrophobic or ionic interactions is preferred to the use of a simple mixture.

It is known that mCRP is soluble in solutions of low ionic strength and that it aggregates in solutions of high ionic strength. "Solution of low ionic strength" means a solution containing ≦0.05M NaCl or a solution of another salt having an equivalent relative salt concentration. "Solution of high ionic strength" means a solution containing >0.05 M NaCl or a solution of another salt having an equivalent relative salt concentration, including physiological solutions (about 0.15 M NaCl or a solution having an equivalent salt concentration). Thus, an immunogen can be associated with an mCRP by providing the mCRP in a low ionic strength solution, adding the immunogen to the solution, and increasing the ionic strength of the solution so that the mCRP aggregates, trapping the immunogen in the aggregates. Thus, the resulting mCRP aggregates will include the immunogen as part of the aggregates. An immunogen can be associated with a mutant-mCRP in this same manner, provided that the amino acid changes in the mutant-mCRP do not substantially change the solubility of the mutant-mCRP as compared to mCRP. Since mCRP has strong hydrophobic characteristics, an immunogen can be associated with most mutant-mCRPs in this manner. The formation of aggregates is the most preferred method of associating an mCRP or a mutant-mCRP with an immunogen.

An immunogen and an mCRP or a mutant-mCRP also can be associated by attaching them both to the surfaces of liposomes. Methods of making liposomes and attaching materials to their surfaces are well known in the art. See, e.g., U.S. Pat. Nos. 5,283,238 and 5,858,399 and references cited therein.

Finally, an immunogen can be associated with an mCRP or a mutant-mCRP by covalent attachment to the mCRP or mutant-mCRP. Methods of covalently attaching compounds to proteins are well known (see above discussion of attaching haptens to carriers).

The mCRP or mutant-mCRP and the immunogen can be administered in any conventional manner, including orally, intradermally, subcutaneously, intramuscularly, nasally, etc. The preferred route of administration for both the immunogen and the mCRP or mutant-mCRP is subcutaneously.

Effective amounts (effective dosages and number of doses) of the mCRP or mutant-mCRP necessary to elicit an enhanced immune response can be determined empirically as is known in the art. It is understood by those skilled in the art that the dose of the mCRP or mutant-mCRP that must be administered will vary depending on, for example, the animal that will receive the mCRP or mutant-mCRP, the route(s) of administration, whether the mCRP or mutant-mCRP and the immunogen are given together or separately, and the age and size of the animal. Generally, a dose of about 0.01 to about 10 mg of an mCRP or a mutant-mCRP per kilogram of body weight of the animal will be effective to enhance an immune response to an immunogen. It is also understood that it likely will be necessary to give more than one dose of the mCRP or mutant-mCRP. If multiple doses must be given to the animal, the interval between doses is preferably about 21 days. Administration of the mCRP or mutant-mCRP should be continued until an acceptable immune response is achieved.

Effective amounts (effective dosages and number of doses) of the immunogens are known in the art or can also be determined empirically. It is understood by those skilled in the art that the dose of immunogen that must be administered will vary depending on, for example, the animal that will receive the immunogen, the route(s) of administration, whether the immunogen and the mCRP or mutant-mCRP are given together or separately, and the age and size of the animal. It is also understood that it may be necessary to give more than one dose of the immunogen. If multiple doses must be given to the animal, the interval between doses is preferably about 21 days. Administration of the immunogen should be continued until an acceptable immune response is achieved.

The invention also provides vaccines comprising an immunogen and an mCRP or a mutant-mCRP in a pharmaceutically-acceptable vehicle. Pharmaceutically-acceptable vehicles are well known in the art. For instance, the vehicle may simply be a liquid, such as saline, buffers or an oil. It could also be a biodegradable polymer, such as poly(lactic/glycolic acid) polymer. Gupta et al., *Dev. Biol. Stand.*, 92, 63–78 (1998); Jones et al., *Behring Inst. Mitt.*, 98, 220–228 (1997). The vaccines can also be provided in lyophilized form and reconstituted with a liquid, such as water or saline, just prior to use. It will be apparent to those persons skilled in the art that certain vehicles may be more preferable depending upon, for instance, the route of administration and the nature of the immunogen employed in the vaccine.

The invention further provides a kit. The kit is a packaged combination of one or more containers holding reagents and other materials useful for immunizing animals. Suitable containers for the reagents include bottles, vials, test tubes, syringes, and other containers known in the art. The kit may comprise one container holding an mCRP or a mutant-mCRP and one container holding an immunogen. Alternatively, the kit may comprise one container holding both an immunogen and the mCRP or mutant-mCRP. The kit may also contain other materials which are known in the art and which may be desirable from a commercial and user standpoint, such as diluents, empty syringes, gauze pads, disinfectant solution, etc.

Surprisingly, by the present invention, an immune response to a hapten can be elicited simply by associating the hapten with an mCRP or a mutant-mCRP. Thus, the need to couple a hapten to a immunogenic carrier may be eliminated. The haptens can be associated with the mCRP or mutant-mCRP in the ways described above for immunogens. When used in association with haptens, the mCRP or mutant-mCRP is preferably, but need not be, immunogenic in the species of animal to be immunized with the hapten in order to obtain increased stimulation of the immune response due to the immunogenicity of the mCRP or mutant-mCRP. Thus, the mCRP or mutant-mCRP is preferably from a species of animal different than the species to be immunized with the hapten. Effective dosages and routes of administration of the hapten and the mCRP or mutant-mCRP can be determined empirically and depend on the criteria described above for immunogens. The invention also provides vaccines comprising a hapten in association with an mCRP or a mutant-mCRP and kits comprising a container holding a hapten in association with an mCRP or a mutant-mCRP.

EXAMPLES

Example 1

Use of mCRP to Enhance the Immune Response to Tetanus Toxoid

Native CRP was isolated from pleural or ascites fluid by calcium-dependent affinity chromatography using phosphorylcholine-substituted BioGel® A 0.5 m (an agarose-based resin obtained from BioRad Laboratories) as described by Volanakis et al. (in *J. Immunol.*, 113:9–17 (1978)) and modified by Potempa et al. (as described in *Mol. Immunol.*, 24:531–41 (1987)). Briefly, the pleural or ascites fluid was passed over the phosphorylcholine-substituted column, and the CRP was allowed to bind. Then, the column was exhaustively washed with 75 mM Tris-HCl-buffered saline (pH 7.2) containing 2 mM $CaCl_2$ until the absorbance at 280 nm was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations. CRP-containing fractions were pooled, diluted three-to-five fold with deionized water, adsorbed to Q-Sepharose Fast Flow® (ion exchange resin (Pharmacia), and then eluted with a linear salt gradient from 0–1 M NaCl in 10 mM Tris-HCl, pH 7.4. CRP-containing fractions were pooled and re-calcified to 2–5 mM $CaCl_2$ (by adding a suitable amount of a 1M solution) and applied to unsubstituted Biogel® A 0.5 m column to remove residual serum amyloid P component ("SAP"). Then, the CRP was concentrated to 1 mg/ml using ultrafiltration (Amicon; PM30 membrane) under 10–20 psi nitrogen. A CRP extinction coefficient (mg/ml) of 1.95 was used to determine concentration. Next, the concentrated CRP was exhaustively dialyzed against 10 mM Tris-HCl-buffered saline, pH 7.2, containing 2 mM $CaCl_2$. This preparation produced a single Mr 23,000 band on SDS-PAGE electrophoresis and was more than 99% free of SAP, IgG and all other proteins tested for antigenically.

To make mCRP, purified native CRP, prepared as described above, at 1 mg/ml was incubated in 8M ultra-pure urea in the presence of 10 mM EDTA for one hour at 37° C. The urea was removed by dialysis into 10 mM sodium phosphate buffer (pH 7.4) or Tris-HCl buffer (pH 7.2) containing 0.015M sodium chloride. The mCRP was sterile filtered through a 0.2 micron filter (Gelman, Ann Arbor, Mich.).

Sterile-filtered mCRP, 600 µg/ml in 25 mM Tris-HCl buffer, pH 7.4, containing 0.015 M NaCl, was diluted to 12.5 µg/ml, 25 µg/ml, or 50 µg/ml in saline (0.15 M NaCl), and 0.1 ml of each mCRP concentration, or 0.1 ml of saline (control), was admixed with 0.1 ml tetanus toxoid at 0.25 µg/ml in saline. The dilution of the mCRP with saline caused the majority of the mCRP to aggregate, trapping the tetanus toxoid in the aggregates, and forming a suspension which was used for immunization.

Ten female mice, 4–6 weeks old, were immunized subcutaneously (s.c.) on day 0 with either the tetanus toxoid-mCRP suspension or with tetanus toxoid in saline. The immunizations were repeated on day 21.

Blood samples were drawn on days 21, 28 and 35, and titers of IgG antibodies to tetanus toxoid were determined by a standard enzyme immunoassay (EIA) using tetanus toxoid immobilized in the wells of a microtiter plate and serial dilutions of the sera from the immunized mice. Binding isotherms were generated, from which 50% binding titers were calculated.

The results are presented in Table 1 below. As can be seen from Table 1, after 4 and 5 weeks, IgG antibodies to tetanus toxoid were increased in all mCRP-treated animals, compared to saline-treated animals. In particular, IgG antibodies were increased 4–6 fold in mCRP-treated animals, compared to saline-treated animals, for the animals receiving 50 µg/ml mCRP. No side effects of administering mCRP were observed.

TABLE 1

EIA Anti-IgG Titers To Tetanus Toxoid

| | | Modified-CRP | | |
|---|---|---|---|---|
| Day blood was drawn | Saline | 12.5 µg/ml | 25 µg/ml | 50 µg/ml |
| 21 | 350 | — | 275 | 350 |
| 28 | 3000 | 4100 | 4200 | 12,800 |
| 35 | 2100 | 3600 | 6000 | 11,200 |

Example 2

Use of Mutant-mCRP to Enhance the Immune Response to Tumor-Specific Peptide Immunogens This example demonstrates the adjuvant activity of a mutant-mCRP in mice receiving immunogenic peptides comprising epitopes of a tumor specific antigen (named Labyrinthin) found on human adenocarcinoma A549 tumor cells. Three peptides were made using standard solid phase synthesis methods. Two of the peptides were ten amino acids in length, and the the third was six amino acids in length. These three peptides have sequences found in the protein region of the antigen recognized by monoclonal antibody 44-3A6. Radosevich et al., *Cancer Res.*, 45, 5808–5812 (1985). A solution of the peptides in saline at 10 µg/ml was prepared.

The mutant-mCRP was prepared as described in U.S. Pat. No. 5,874,238, the complete disclosure of which is incorporated herein by reference, by culturing *Escherichia coli* BLR(DE3) transformed with plasmid pIT 13 (see Example 1, particularly sections F–H, of U.S. Pat. No. 5,874,238). Plasmid pIT13 comprises DNA coding for a mutant human CRP subunit which has the same sequence as an unmutated human CRP subunit, except that it has a methionine added at the N-terminal and the two cysteines at positions 36 and 97 have been replaced by alanines.

Groups of 5 mice were injected subcutaneously (s.c.) on day 1 with 100 µl of the solution of the peptides in saline on the right hindquarter and with either 100 µl of the mutant-mCRP (200 µg) or 100 µl saline on the opposite (left) hindquarter. Starting on day 7, and continuing once per week for 10 weeks, the mice were given additional 100 µl s.c. injections of the mutant-mCRP or saline on the left hindquarter.

Sera were collected at various times over a 12-week period. The blood was microfuged, the serum removed, and 1 µl of saturated sodium azide was added to each serum sample. The sera were stored at 4° C. until used.

The sera were assayed by EIA for IgG immunoreactivity to a cell lysate of A549 human adenocarcinoma cells. A549 cells were obtained from the ATCC and grown in RPMI-1640 (90%), fetal calf serum (10%), with supplements, under standard conditions. A549 cells abundantly express the antigen recognized by the monoclonal antibody 44-3A6. Confluent flasks were harvested by scraping the cells, washing them three times with sterile saline, and adjusting the cells to $1 \times 10^6$ cells/ml. The cells were then sonicated (3 pulses for 15 seconds on ice). 50 µl of this lysate was put in each microtiter plate (Costar) for 30 minutes. 50 µl of 1.0% EM grade glutaraldehyde was then added to each well for 30 minutes. The fluid was then removed, and the well flooded with 1% RIA grade bovine serum albumin, for 30 minutes. Plates were stored at 4° C. in BSA/saline with azide. The mouse sera were diluted 1:200 in saline (with azide), and 50 µl aliquots were incubated in plates of A549 lysates for one hour. After washing the plates, a secondary antimouse antibody (alkaline phosphatase conjugated) was added and the plates were incubated for 1–3 hours. Substrate was added after washing the plates. Readings were taken after 2 hours, at 405 nm.

Figure 1B:
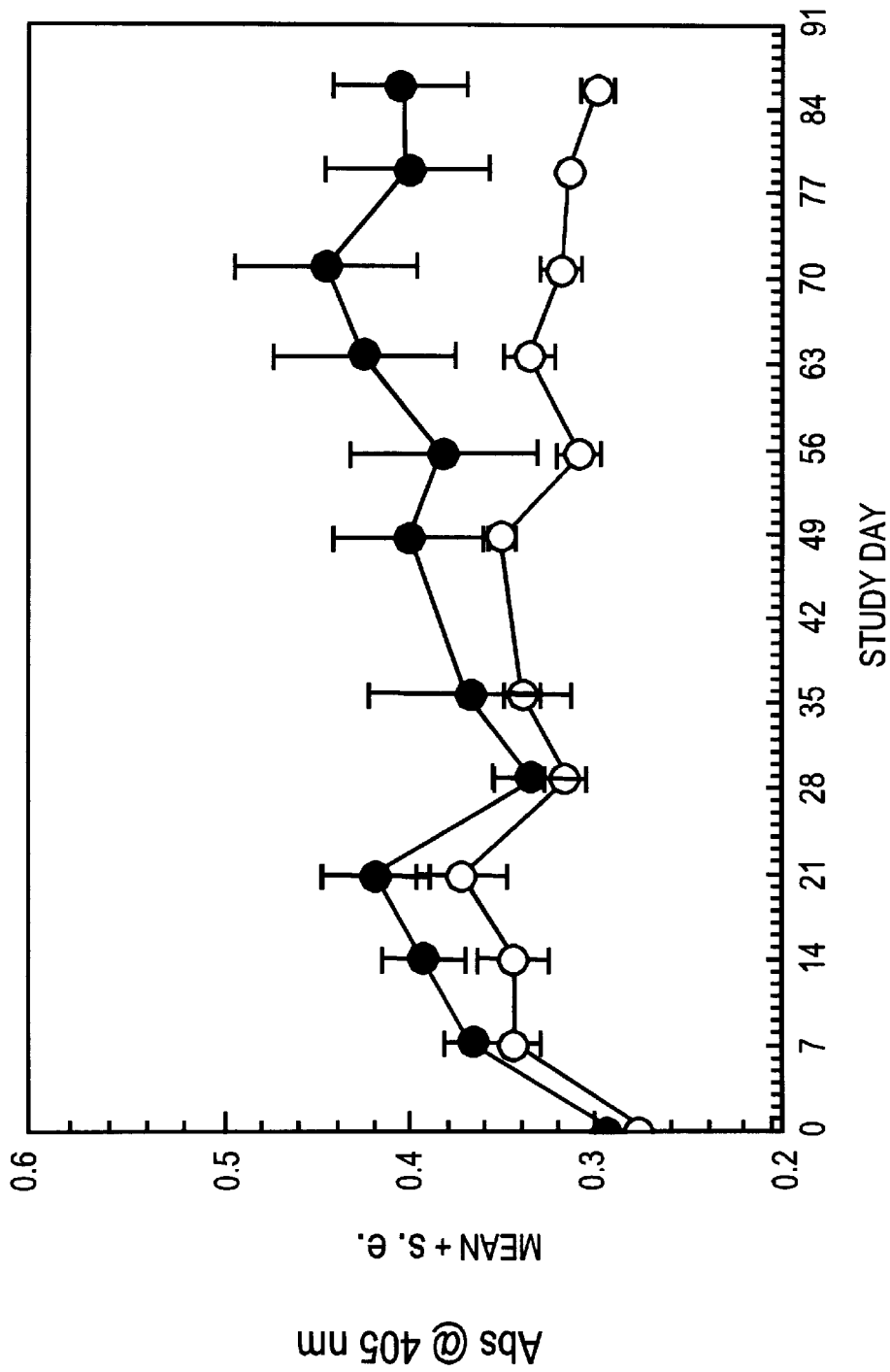
FIG. 1B: Graph of absorbance at 405 nm versus study day for mice immunized with human lung adenocarcinoma A-549 peptides with mutant-mCRP (treated group) or with saline (no mutant-mCRP; control group). Open circles—control group; closed circles—mutant-mCRP-treated group.
Figure 1C:
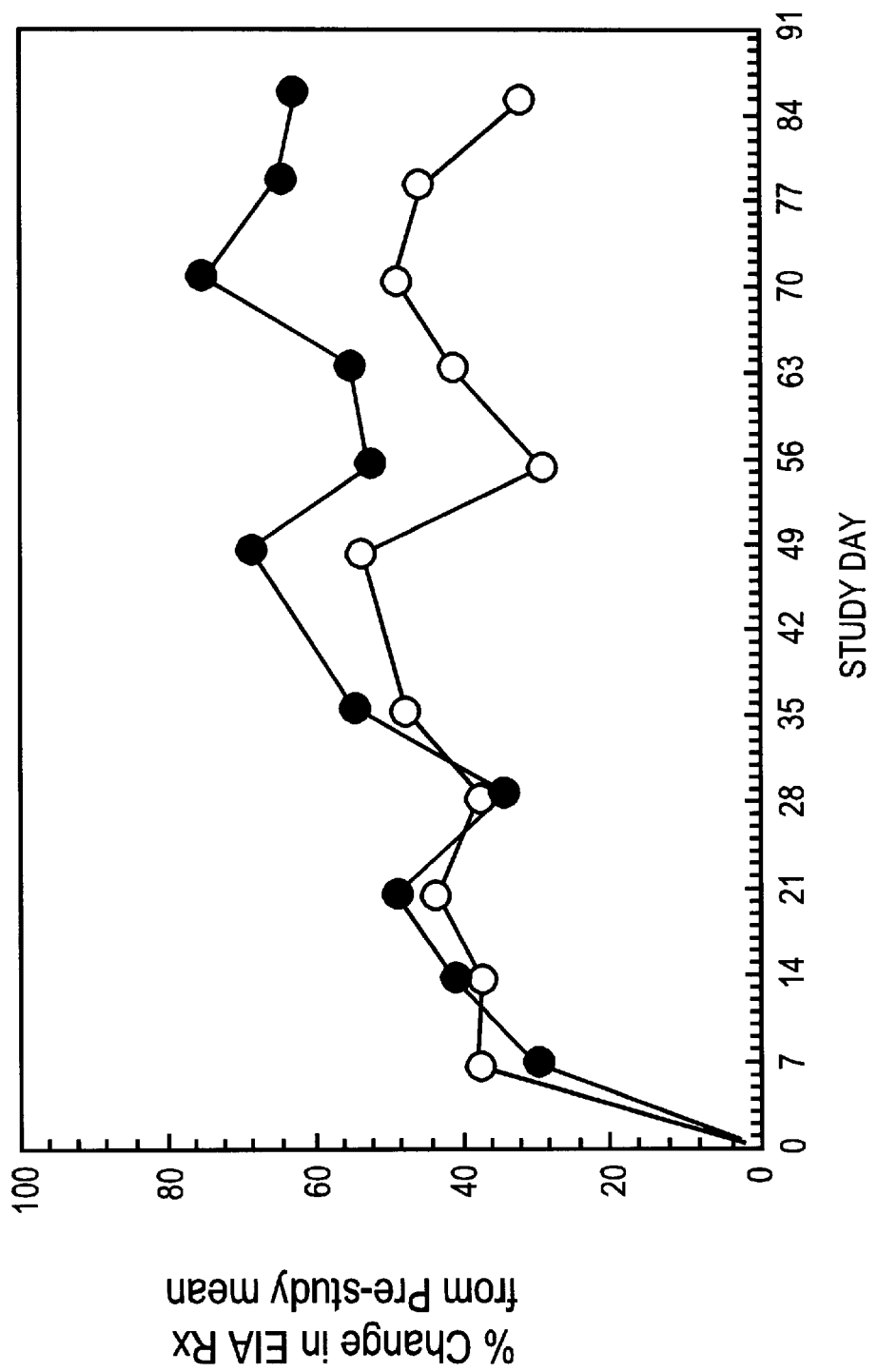
FIG. 1C: Graph of % change in enzyme immunoassay (EIA) reactivity (Rx) versus study day for mice immunized with human lung adenocarcinoma A-549 peptides with mutant-mCRP (treated group) or with saline (no mutant-mCRP; control group). Open circles—control group; closed circles—mutant-mCRP-treated group.
Figure 1D:
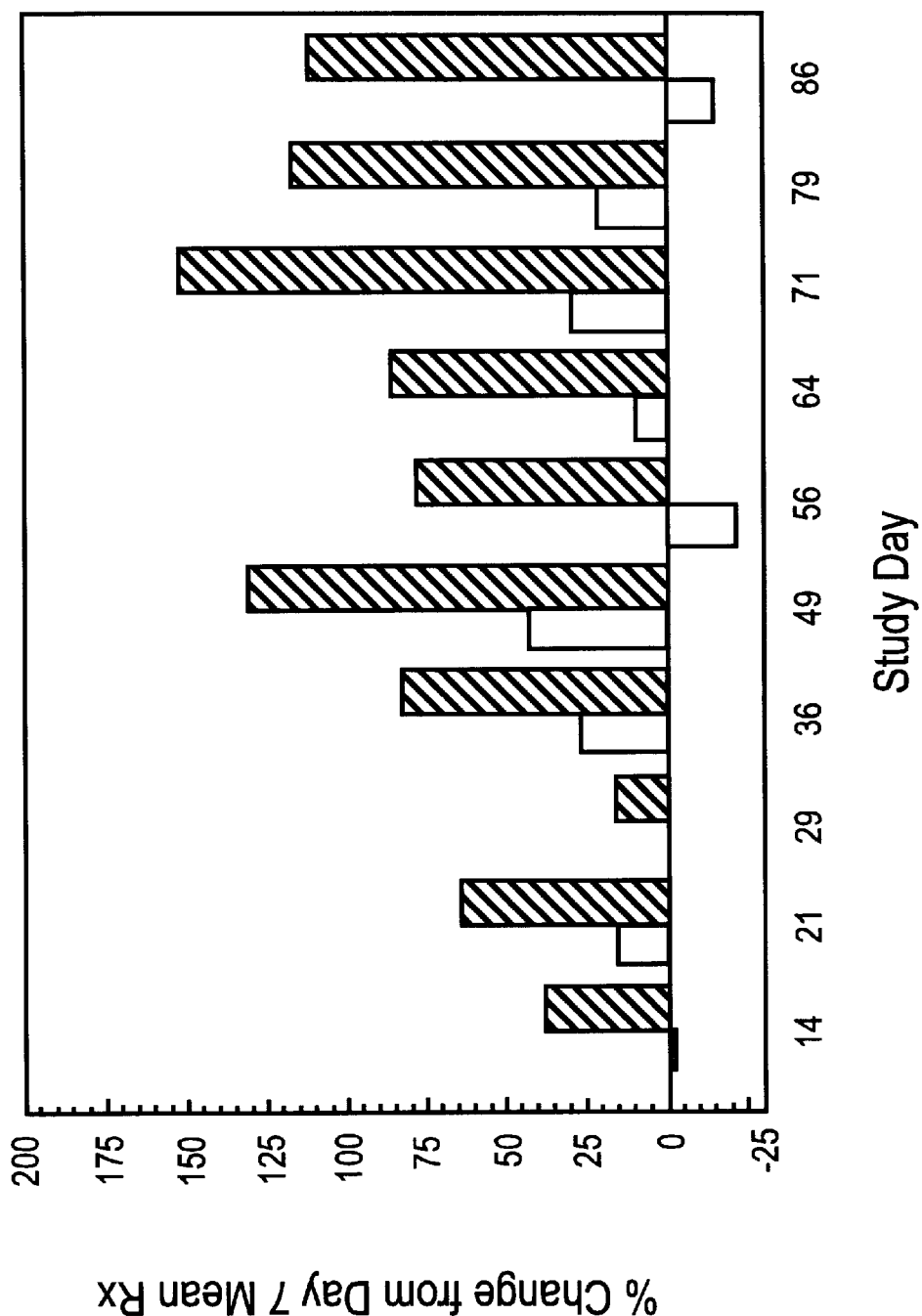
FIG. 1D: Graph of % change from seven-day mean EIA Rx versus study day for mice immunized with human lung adenocarcinoma A-549 peptides with mutant-mCRP (treated group) or with saline (no mutant-mCRP; control group). Open bars—control group; closed bars—mutant-mCRP-treated group.

The results are presented in FIGS. 1A–D. In FIGS. 1A–B, the data are plotted as mean± standard error of group reactivity (FIG. 1A and FIG. 1B show data from two different experiments). The data were compared by calculating the mean change on test dates from the pre-study mean for that group of animals (FIG. 1C). The data were also compared by calculating the mean change on all test dates from that level of reactivity noted on day 7 (one week after the initial immunization) (FIG. 1D). As can be seen in FIGS. 1A–D, the human mutant-mCRP enhanced the mouse IgG immune response to human adenocarcinoma-specific peptide antigens. The enhanced anti-adenocarcinoma immune response increased above control after about 7–8 weeks, and persisted at the elevated level up until at least week 12. After defining the initial titers to the adenocarcinoma antigens on day 7, mutant-mCRP booster injections (with no further injections of antigens) led to continued increases in the mouse IgG response to adenocarcinoma-specific antigens. After 7–8 weeks, IgG titers against adenocarcinoma antigen showed steady increases in the mutant-mCRP-treated experimental group.

The multiple subcutaneous injections of mutant-mCRP were safely tolerated with no noted side effects. However, on study days 14 and 21, days when the second and third mutant-mCRP booster injections were given, a mild darkening of the skin was observed in mutant-mCRP-treated animals at the spot where the peptides were initially injected. No darkening of the skin was observed in the saline-treated animals or at the site of the mutant-mCRP injections. This darkening of the skin around the primary immunization site may also be an indication of the enhanced immune response of the mutant-mCRP-treated mice to the immunogens.

We claim:

1. A method of eliciting an immune response to a hapten in an animal comprising administering to the animal an effective amount of the hapten in association with an effective amount of a modified C-reactive protein (mCRP) or a mutant-mCRP.

2. The method of claim 1 wherein at least some of the mCRP or the mutant-mCRP and some of the hapten are present together in aggregates.

* * * * *

UNITED STATES PATENT AND TRADEMARK OFFICE
CERTIFICATE OF CORRECTION

PATENT NO. : 6,190,670 B1
DATED : February 20, 2001
INVENTOR(S) : Potempta et al.

It is certified that error appears in the above-identified patent and that said Letters Patent is hereby corrected as shown below:

<u>Title page,</u>
(60) after "Apr"., delete "2" and add -- 12 -- therefor

Signed and Sealed this

Twenty-eighth Day of August, 2001

Attest:

*Nicholas P. Godici*

NICHOLAS P. GODICI
*Attesting Officer*       *Acting Director of the United States Patent and Trademark Office*